US007247476B2

(12) United States Patent
Young et al.

(10) Patent No.: US 7,247,476 B2
(45) Date of Patent: Jul. 24, 2007

(54) INDIVIDUALIZED ANTI-CANCER ANTIBODIES

(75) Inventors: David S. F. Young, Toronto (CA); Miyoko Takahashi, Toronto (CA)

(73) Assignee: Arius Research Inc., Toronto, Ontario (CA)

(*) Notice: Subject to any disclaimer, the term of this patent is extended or adjusted under 35 U.S.C. 154(b) by 29 days.

(21) Appl. No.: 11/241,721

(22) Filed: Sep. 30, 2005

(65) Prior Publication Data
US 2006/0073153 A1 Apr. 6, 2006

Related U.S. Application Data

(60) Continuation of application No. 10/226,716, filed on Aug. 22, 2002, now abandoned, which is a continuation of application No. 09/727,370, filed on Nov. 29, 2000, now abandoned, which is a division of application No. 09/415,278, filed on Oct. 8, 1999, now Pat. No. 6,180,357.

(51) Int. Cl.
C12N 5/06 (2006.01)
(52) U.S. Cl. .............. 435/332; 530/387.3; 530/388.1; 530/391.7
(58) Field of Classification Search ............ 435/332; 530/387.3, 388.1, 391.7
See application file for complete search history.

(56) References Cited

U.S. PATENT DOCUMENTS

| 4,172,124 | A | 10/1979 | Koprowski et al. |
| 4,861,581 | A | 8/1989 | Epstein et al. |
| 4,939,240 | A | 7/1990 | Chu |
| 5,171,665 | A | 12/1992 | Hellstrom et al. |
| 5,484,596 | A | 1/1996 | Hanna, Jr. et al. |
| 5,693,363 | A | 12/1997 | Kuroda et al. |
| 5,750,102 | A | 5/1998 | Eisenbach et al. |
| 5,780,033 | A | 7/1998 | Torchilin et al. |
| 5,783,186 | A | 7/1998 | Arakawa et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |

FOREIGN PATENT DOCUMENTS

| EP | 0 222 360 | 5/1987 |
| WO | WO 94/18345 | 8/1994 |

OTHER PUBLICATIONS

C. Badger et al., "Prospects for Monoclonal Antibody therapy of Leukimia and Lymphoma", Cancer vol. 58, (1986) pp. 584-589.
A. Begg et al., "Rapid Fluorescence-based Assay for Radiosensitivity and Chemoscensivity Testing in mammalian Cells in Vitro", Cancer research, vol. 49, (1986) pp. 565-569.
E. Boven et al., "Monoclonal Antibodies in Cancer Treatment: Where Do We Stand After 10 Years?", Radiotherapy & Oncology, vol. 5 (1986) pp. 109-117.
A. Costa et al., "Implications of Disaggggregation Procedures on Biological Representation of Human Solid Tumours", Cell Tissue Kinet, vol. 20, (1987) pp. 171-180.
Cruse et al., Illustrated Dictionary of Immunology, CRC Press, (1995)p. 280.
S. Dairkee et al., "Partial Enxymatic Degredation of Stroma Allows Enrichment and Expansion of Primary Breast Tumor Cells", Cancer Res. vol. 57. (1997) pp. 1590-1596.
R. Dillman, "Antibodies as Cytotoxic Therapy", Journal of Clinical Oncology, vol. 12, (1994) pp. 1497-1515.
R. Dillman, "Monoclonal Antibodies for Treating Cancer", Annals of Internal Medecine, vol. 111 (1989)pp. 592-603.
M. Disis et al., "Her-2/neu Protein: A Target for Antigen-Specicfc Immunotherapy of Human Cancer", Advances in Cancer Research, vol. 71 (1997) pp. 343-371.
H. Dvorak et al., "Structure of Solid Tumors and their Vasculature: Implications for Therapy With Monoclonal Antibodies", Cancer Cells, vol. 3 (1991) pp. 77-85.
S. Engelhohn et al., "Disaggregation of Human Solid Tumours by Combined Mechanical and Enzymatic methods", Br. J. Cancer vol. 51 (1985) pp. 93-98.
A. Epsstein et al., "Two New Monoclonal Antibodies: Lym-1 and Lyn02, Reactive with Human B-Lymphocytes and Derived Tumours, with Immunodiagnostic and Immunotherapeutic Potential", Cancer research vol. 47 (1987) pp. 830-840.
K. Foon, "Biological Therapy of Cancer", Breast Cancer Research & Treatmetn vol. 7 (1986) pp. 5-14.
B. Franzen et al., "Nonenzymatic Extraction of Cells from Clnical Tumor Material for Analysis of Gene Expression by Two-Dimensional Polyacrylaamide gel Electrophoresis", Electrophoresis, vol. 14 (1993) pp. 1045-1053.

(Continued)

*Primary Examiner*—Stephen L. Rawlings
*Assistant Examiner*—Brad Duffy
(74) *Attorney, Agent, or Firm*—McHale & Slavin, P.A.

(57) ABSTRACT

The present invention relates to a method for producing patient specific anti-cancer antibodies using a novel paradigm of screening. By segregating the anti-cancer antibodies using cancer cell cytotoxicity as an end point, the process makes possible the production of anti-cancer antibodies customized for the individual patient that can be used for therapeutic and diagnostic purposes. The invention further relates to the process by which the antibodies are made and to their methods of use. The antibodies can be made specifically for one tumor derived from a particular patient and are selected on the basis of their cancer cell cytotoxicity and simultaneous lack of toxicity for non-cancerous cells. The antibodies can be used in aid of staging and diagnosis of a cancer, and can be used to treat tumor metastases. The anti-cancer antibodies can be conjugated to red blood cells obtained from that patient and re-infused for treatment of metastases based upon the recognition that metastatic cancers are usually well vascularized and the delivery of anti-cancer antibodies by red blood cells can have the effect of concentrating the antibodies at the site of the tumor.

6 Claims, No Drawings

OTHER PUBLICATIONS

D. Harris et al., "Serotherapy of Cancer", Seminars in Oncology, vol. 16 (1989) pp. 180-198.

Herlyn et al., "Monoclonal Anticolon Carcinoma Antibodies in Complement-Dependent Cytoxicity", Int. J. Cancer 27, (1981); pp. 769-774.

Holz E et al., "Antibody-Based immunotherapeutic Strategies in Colorectal Cancer", Recent Results in Cancer Research, vol. 142 (1996) pp. 381-400.

Horoszewicz et al., "Monoclonal Antibodies to a New Antigenic Marker in Epithelial Prostatic Cells and Serum of Prostatic Cancer Patients", Anticancer Research 7, (1987) pp. 927-936.

V. Kravstov et al., "Automated monitoring of Apoptosis in Suspension Cell Cultures", Laboratory Investigation, vol. 74 (1996) pp. 557-570.

A. Knuth et al, "ADCC reactivity of human melanoma cells with mouse monoclonal antibodies", Proc. Am. Assoc. Cancer Res., 25:1005 (May 1984).

INDIVIDUALIZED ANTI-CANCER ANTIBODIES

REFERENCE TO RELATED APPLICATIONS

This application is a continuation of application Ser. No. 10/226,716, filed Aug. 22, 2002, now abandoned which is a continuation of application Ser. No. 09/727,370, filed Nov. 29, 2000, now abandoned which is a divisional of application Ser. No. 09/415,278, filed Oct. 8, 1999, now U.S. Pat. No. 6,180,357, the contents of which are herein incorporated by reference.

FIELD OF THE INVENTION

This invention relates to the production of anti-cancer antibodies customized for the individual patient that can be used for therapeutic and diagnostic purposes. The invention further relates to the process by which the antibodies are made and to their methods of use.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment can not be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

At the present time, however, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-her 2 antibody in combination with Cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only one patient having a partial response. In other trials, use of 17-1A produced only one complete response and two minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibody for melanoma. Thus, it can be seen that despite successful small animal studies that are a prerequisite for human clinical trials, the antibodies that have been tested have been for the most part ineffective.

Prior Patents

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for producing a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

This application teaches a method for producing patient specific anti-cancer antibodies using a novel paradigm of screening. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing anti-cancer antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated.

In addition to anti-cancer antibodies, the patient can elect to receive the currently recommended therapies as part of a multi-modal regimen of treatment. The fact that the antibodies isolated via the present methodology are relatively non-toxic to non-cancerous cells allow combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated red blood cells can be effective against in situ tumors, too. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that effectively its function is lost.

Accordingly, it is an objective of the invention to teach a method for producing anti-cancer antibodies from cells derived from a particular individual which are cytotoxic with respect to cancer cells while simultaneously being relatively non-toxic to non-cancerous cells.

It is an additional objective of the invention to produce novel anti-cancer antibodies.

It is a further objective of the instant invention to produce anti-cancer antibodies whose cytotoxicity is mediated through antibody dependent cellular toxicity.

It is yet an additional objective of the instant invention to produce anti-cancer antibodies whose cytotoxicity is mediated through complement dependent cellular toxicity.

It is still a further objective of the instant invention to produce anti-cancer antibodies whose cytotoxicity is a function of their ability to catalyze hydrolysis of cellular chemical bonds.

Still an additional objective of the instant invention is to produce anti-cancer antibodies useful as a vaccine to produce an immune response against putative cancer antigen residing on tumor cells.

A further objective of the instant invention is the use of antibodies to target cell membrane proteins, such as growth receptors, cell membrane pumps and cell anchoring proteins, thereby interfering with or down regulating their function.

Yet an additional objective of the instant invention is the production of anti-cancer antibodies whose cell-killing utility is concomitant with their ability to effect a conformational change in cellular proteins such that a signal will be transduced to initiate cell-killing.

A still further objective of the instant invention is to produce anti-cancer antibodies which are useful for diagnosis, prognosis, and monitoring of cancer, e.g. production of a panel of therapeutic anti-cancer antibodies to test patient samples to determine if they contain any suitable antibodies for therapeutic use.

Yet another objective of the instant invention is to produce novel antigens, associated with cancer processes, which can be discovered by using anti-cancer antibodies derived by the process of the instant invention. These antigens are not limited to proteins, as is generally the case with genomic data; they may also be derived from carbohydrates or lipids or combinations thereof.

Other objects and advantages of this invention will become apparent from the following description wherein are set forth, by way of illustration and example, certain embodiments of this invention.

DETAILED DESCRIPTION OF THE INVENTION

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification.

One of the potential benefits of monoclonal antibodies with respect to the treatment of cancer is their ability to specifically recognize single antigens. It was thought that in some instances cancer cells possess antigens that were specific to that kind of transformed cell. It is now more frequently believed that cancer cells have few unique antigens, rather, they tend to over-express a normal antigen or express fetal antigens. Nevertheless, the use of monoclonal antibodies provided a method of delivering reproducible doses of antibodies to the patient with the expectation of better response rates than with polyclonal antibodies.

Traditionally, monoclonal antibodies have been made according to fundamental principles laid down by Kohler and Milstein. Mice are immunized with antigens, with or without, adjuvants. The splenocytes are harvested from the spleen for fusion with immortalized hybridoma partners. These are seeded into microtitre plates where they can secrete antibodies into the supernatant that is used for cell culture. To select from the hybridomas that have been plated for the ones that produce antibodies of interest the hybridoma supernatants are usually tested for antibody binding to antigens in an ELISA (enzyme linked immunosorbent assay) assay. The idea is that the wells that contain the hybridoma of interest will contain antibodies that will bind most avidly to the test antigen, usually the immunizing antigen. These wells are then subcloned in limiting dilution fashion to produce monoclonal hybridomas. The selection for the clones of interest is repeated using an ELISA assay to test for antibody binding. Therefore, the principle that has been propagated is that in the production of monoclonal antibodies the hybridomas that produce the most avidly binding antibodies are the ones that are selected from among all the hybridomas that were initially produced. That is to say, the preferred antibody is the one with highest affinity for the antigen of interest.

There have been many modifications of this procedure such as using whole cells for immunization. In this method, instead of using purified antigens, entire cells are used for immunization. Another modification is the use of cellular ELISA for screening. In this method instead of using purified antigens as the target in the ELISA, fixed cells are used. In addition to ELISA tests, complement mediated cytotoxicity assays have also been used in the screening process. However, antibody-binding assays were used in conjunction with cytotoxicity tests. Thus, despite many modifications, the process of producing monoclonal antibodies relies on antibody binding to the test antigen as an endpoint.

Most antibodies directed against cancer cells have been produced using the traditional methods outlined above. These antibodies have been used both therapeutically and diagnostically. In general, for both these applications, the antibody has been used as the targeting agent that delivers a payload to the site of the cancer. These antibody conjugates can either be radioactive, toxic, or serve as an intermediary for further delivery of a drug to the body, such as an enzyme or biotin. Furthermore, it was widely held, until recently, that naked antibodies had little effect in vivo. Both HERCEPTIN and RITUXIMAB are humanized murine monoclonal antibodies that have recently been approved for human use by the FDA. However, both these antibodies were initially made by assaying for antibody binding and their direct cytotoxicity was not the primary goal during the production of hybridomas. Any tendency for these antibodies to produce tumor cell killing is thus through chance, not by design.

Although the production of monoclonal antibodies have been carried out using whole cell immunization for various applications the screening of these hybridomas have relied on either putative or identified target antigens or on the selectivity of these hybridomas for specific tissues. It is axiomatic that the best antibodies are the ones with the highest binding constants. This concept originated from the basic biochemical principle that enzymes with the highest binding constants were the ones that were the most effective for catalyzing a reaction. This concept is applicable to receptor ligand binding where the drug molecule binding to the receptor with the greatest affinity usually has the highest probability for initiating or inhibiting a signal. However, this may not always be the case since it is possible that in certain situations there may be cases where the initiation or inhibition of a signal may be mediated through non-receptor binding. The information conveyed by a conformational change induced by ligand binding can have many consequences such as a signal transduction, endocytosis, among the others. The ability to produce a conformational change in a receptor molecule may not necessarily be due to the filling of a ligand receptor pocket but may occur through the binding of another extra cellular domain or due to receptor clustering induced by a multivalent ligand.

The production of antibodies to produce cell killing need not be predicated upon screening of the hybridomas for the best binding antibodies. Rather, although not advocated by those who produce monoclonal antibodies, the screening of the hybridoma supernatants for cell killing or alternatively for cessation of growth of the cancerous cells may be selected as a desirable endpoint for the production of cytotoxic or cytostatic antibodies. It is well understood that the in-vivo antibodies mediate their function through the Fc portions and that the utility of the therapeutic antibody is determined by the functionality of the constant region or attached moieties. In this case the FAb portion of the antibody, the antigen-combining portion, will confer to the antibody its specificity and the Fc portion its functionality. The antigen combining site of the antibody can be considered to be the product of a natural combinatorial library. The result of the rearrangement of the variable region of the antibody can be considered a molecular combinatorial library where the output is a peptide. Therefore, the sampling of this combinatorial library can be based on any parameter. Like sampling a natural compound library for antibiotics, it is possible to sample an antibody library for cytotoxic or cytostatic compounds.

The various endpoints in a screen must be differentiated from each other. For example, the difference between antibody binding to the cell is distinct from cell killing. Cell killing (cytotoxicity) is distinct from the mechanisms of cell death such as oncosis or apoptosis. There can be many processes by which cell death is achieved and some of these can lead either to oncosis or apoptosis. There is speculation that there are other cell death mechanisms other than oncosis or apoptosis but regardless of how the cell arrives at death there are some commonalities of cell death. One of these is the absence of metabolism and another is the denaturation of enzymes. In either case vital stains will fail to stain these cells. These endpoints of cell death have been long understood and predate the current understanding of the mechanisms of cell death. Furthermore, there is the distinction between cytotoxic effects where cells are killed and cytostatic effects where the proliferation of cells are inhibited.

In a preferred embodiment of the present invention, the assay is conducted by focusing on cytotoxic activity toward cancerous cells as an end point. In a preferred embodiment, a live/dead assay kit, for example the LIVE/DEAD® Viability/Cytotoxicity Assay Kit (L-3224) by Molecular Probes, is utilized. The Molecular Probes kit provides a two-color fluorescence cell viability assay that is based on the simultaneous determination of live and dead cells with two probes that measure two recognized parameters of cell viability—intracellular esterase activity and plasma membrane integrity. The assay principles are general and applicable to most eukaryotic cell types, including adherent cells and certain tissues, but not to bacteria or yeast. This fluorescence-based method of assessing cell viability is preferred in place of such assays as trypan blue exclusion, Cr release and similar methods for determining cell viability and cytotoxicity.

In carrying out the assay, live cells are distinguished by the presence of ubiquitous intracellular esterase activity, determined by the enzymatic conversion of the virtually nonfluorescent cell-permeant CALCEIN AM to the intensely fluorescent Calcein. The polyanionic dye Calcein is well retained within live cells, producing an intense uniform green fluorescence in live cells (ex/em ~495 nm/~515 nm). EthD-1 enters cells with damaged membranes and undergoes a 40-fold enhancement of fluorescence upon binding to nucleic acids, thereby producing a bright red fluorescence in dead cells (ex/em ~495 nm/~635 nm). EthD-1 is excluded by the intact plasma membrane of live cells. The determination of cell viability depends on these physical and biochemical properties of cells. Cytotoxic events that do not affect these cell properties may not be accurately assessed using this method. Background fluorescence levels are inherently low with this assay technique because the dyes are virtually nonfluorescent before interacting with cells.

In addition to the various endpoints for screening, there are two other major characteristics of the screening process. The library of antibody gene products is not a random library but is the product of a biasing procedure. In the examples below, the biasing is produced by immunizing mice with fixed cells. This increases the proportion of antibodies that have the potential to bind the target antigen. Although immunization is thought of as a way to produce higher affinity antibodies (affinity maturation) in this case it is not. Rather, it can be considered as a way to shift the set of antigen combining sites towards the targets. This is also distinct from the concept of isotype switching where the functionality, as dictated by the constant portion of the heavy chain, is altered from the initial IgM isotype to another isotype such as IgG.

The third key feature that is crucial in the screening process is the use of multitarget screening. To a certain extent specificity is related to affinity. An example of this is the situation where an antigen has very limited tissue distribution and the affinity of the antibody is a key determinant of the specificity of the antibody—the higher the affinity the more tissue specific the antibody and likewise an antibody with low affinity may bind to tissues other than the one of interest. Therefore, to address the specificity issue the antibodies are screened simultaneously against a variety of cells. In the examples below the hybridoma supernatants (representing the earliest stages of monoclonal antibody development), are tested against a number of cell lines to establish specificity as well as activity.

The antibodies are designed for therapeutic treatment of cancer in patients. Ideally the antibodies can be naked antibodies. They can also be conjugated to toxins. They can be used to target other molecules to the cancer. e.g. biotin conjugated enzymes. Radioactive compounds can also be used for conjugation.

The antibodies can be fragmented and rearranged molecularly. For example Fv fragments can be made; sFv-single chain Fv fragments; diabodies etc.

It is envisioned that these antibodies can be used for diagnosis, prognosis, and monitoring of cancer. For example the patients can have blood samples drawn for shed tumor antigens which can be detected by these antibodies in different formats such as ELISA assays, rapid test panel formats etc. The antibodies can be used to stain tumor biopsies for the purposes of diagnosis. In addition a panel of therapeutic antibodies can be used to test patient samples to determine if there are any suitable antibodies for therapeutic use.

EXAMPLE 1

In order to produce monoclonal antibodies specific for a tumor sample the method of selection of the appropriate hybridoma wells is complicated by the probability of selecting wells which will produce false positive signals. That is to say that there is the likelihood of producing antibodies that can react against normal cells as well as cancer cells. To obviate this possibility one strategy is to mask the anti-normal antigen antibodies from the selection process. This can be accomplished by removing the anti-normal antibodies at the first stage of screening thereby revealing the presence of the desired antibodies. Subsequent limiting dilution cloning can delineate the clones that will not produce killing of control cells but will produce target cancer cell killing.

Biopsy specimens of breast, melanoma, and lung tumors were obtained and stored at −70° C. until used. Single cell suspensions were prepared and fixed with −30° C., 70% ethanol, washed with PBS and reconstituted to an appropriate volume for injection. Balb/c mice were immunized with $2.5 \times 10^5$-$1 \times 10^6$ cells and boosted every third week until a final pre-fusion boost was performed three days prior to the splenectomy. The hybridomas were prepared by fusing the isolated splenocytes with Sp2/0 and NS1 myeloma partners. The supernatants from the fusions were tested for subcloning of the hybridomas.

Cells (including A2058 melanoma cells, CCD-12CoN fibroblasts, MCF-12A breast cells among others) were obtained from ATCC and cultured according to enclosed instructions. The HEY cell line was a gift from Dr. Inka Brockhausen. The non-cancer cells, e.g. CCD-12CoN fibroblasts and MCF-12A breast cells, were plated into 96-well microtitre plates (NUNC) 1 to 2 weeks prior to screening. The cancer cells, e.g. HEY, A2058, BT 483, and HS294t, were plated two or three days prior to screening.

The plated normal cells were fixed prior to use. The plates were washed with 100 microliters of PBS for 10 minutes at room temperature and then aspirated dry. 75 microliters of 0.01 percent glutaraldehyde diluted in PBS were added to each well for five minutes and then aspirated. The plates were washed with 100 microliters of PBS three times at room temperature. The wells were emptied and 100 microliters of one percent human serum albumin in PBS was added to each well for one hour at room temperature. The plates were then stored at four degrees Celsius.

Prior to the transfer of the supernatant from the hybridoma plates the fixed normal cells were washed three times with 100 microliters of PBS at room temperature. After aspiration to the microliters of the primary hybridoma culture supernatants were transferred to the fixed cell plates and incubated for two hours at 37 degrees Celsius in a 8 percent $CO_2$ incubator. The hybridoma supernatants derived from melanoma was incubated with CCD-12 CoN cells and those derived from breast cancer were incubated with MCF-12a cells.

After incubation the absorbed supernatant was divided into two 75 microliter portions and transferred to target cancer cell plates. Prior to the transfer the cancer cell plates were washed three times with 100 microliters of PBS. The supernatant from the CCD-12 CoN cells were transferred to the A2058 and the HS294t cells, whereas the supernatant from MCF-12A cells were transferred to the HEY and BT 483 cells. The cancer cells were incubated with the hybridoma supernatants for 18 hours at 37 degrees Celsisu in an 8 percent $CO_2$ incubator.

The Live/Dead cytotoxicity assay was obtained from Molecular Probes (Eu, Oreg.). The assays were performed according to the manufacturer's instructions with the changes outlined below. The plates with the cells were washed once with 100 microliters of PBS at 37° C. 75 to 100 microliters of supernatant from the hybridoma microtitre plates were transferred to the cell plates and incubated in a 8% $CO_2$ incubator for 18-24 hours. Then, the wells that served as the all dead control were aspirated until empty and 50 microliters of 70% ethanol was added. The plate was then emptied by inverting and blotted dry. Room temperature PBS was dispensed into each well from a multichannel squeeze bottle, tapped three times, emptied by inversion and then blotted dry. 50 microliters of the fluorescent Live/Dead dye diluted in PBS was added to each well and incubated at 37° C. in a 5% $CO_2$ incubator for one hour. The plates were read in a Perkin-Elmer™ HTS7000 fluorescence plate reader and the data was analyzed in Microsoft Excel™.

Four rounds of screening were conducted to produce single clone hybridoma cultures. For two rounds of screening the hybridoma supernatants were tested only against the cancer cells. In the last round of screening the supernatant was tested against a number of non-cancer cells as well as the target cells indicated in table 1. The antibodies were isotyped using a commercial isotyping kit.

A number of monoclonal antibodies were produced in accordance with the method of the present invention. These antibodies, whose characteristics are summarized in Table 1, are identified as 3BD-3, 3BD-6, 3BD-8, 3BD-9, 3BD-15, 3BD-25, 3BD-26 and 3BD-27. Each of the designated antibodies is produced by a hybridoma cell line having an ATCC Accession Number as follows: Antibody ATCC Accession Number

| Antibody | ATCC Accession Number |
|---|---|
| 3BD-8 | PTA-2696 |
| 3BD-26 | PTA-2695 |
| 3BD-27 | PTA-2698 |

These antibodies are considered monoclonal after four rounds of limiting dilution cloning. The anti-melanoma antibodies did not produce significant cancer cell killing. The panel of anti-breast cancer antibodies killed 32-87% of the target cells and <1-3% of the control cells. The predominant isotype was IgG1 even though it was expected that the majority of anti-tumor antibodies would be directed against carbohydrate antigens, and thus, be of the IgM type. There is a high therapeutic index since most antibodies spare the control cells from cell death.

The hybridoma cell lines 3BD-8, 3BD-26 and 3BD-27 were deposited, in accordance with the Budapest Treaty, with the American Type Culture Collection (ATCC), 10801 University Blvd., Manassas, Va. 20110-2209 on Nov. 21, 2000 under Accession Number PTA2696, PTA2695, and PTA2698 respectively. In accordance with 37 CFR 1.808, the depositors assure that all restrictions imposed on the availability to the public of the deposited materials will be irrevocably removed upon the granting of a patent. The depositors additionally assure that the deposited materials will be replaced if viable samples cannot be dispensed by the depository.

TABLE 1

Anti-Breast Cancer Antibodies

% Cell Death

| Clones | Target for Anti-Breast Cancer Antibodies (HEY & A2058) | Normal Fibroblast Cells (CCD-12CoN) | Fibrocystic Breast Cells (MCF-12A) | Isotype |
|---|---|---|---|---|
| 3BD-3 | 74.9% | 3.7% | <1% | γ1, λ |
| 3BD-6 | 68.5% | 5.6% | <1% | γ1, λ |
| 3BD-8 | 81.9% | 4.5% | 2.6% | γ1, κ |
| 3BD-9 | 77.2% | 7.9% | <1% | γ1, λ |
| 3BD-15 | 87.1% | <1% | <1% | γ1, λ |
| 3BD-26 | 54.8% | 3.3% | <1% | μ, κ |
| 3BD-25 | 32.4% | 3.6% | <1% | γ1, κ |
| 3BD-27 | 60.1% | 8.3% | 1.3% | γ1, κ |

EXAMPLE 2

In this example customized anti-cancer antibodies are produced by first obtaining samples of the patient's tumor. Usually this is from a biopsy specimen from a solid tumor or a blood sample from hematogenous tumors. The samples are prepared into single cell suspensions and fixed for injection into mice. After the completion of the immunization schedule the hybridomas are produced from the splenocytes. The hybridomas are screened against a variety of cancer cell lines and normal cells in standard cytotoxicity assays. Those hybridomas that are reactive against cancer cell lines but are not reactive against normal non-transformed cells are selected for further propagation. Clones that were considered positive were ones that selectively killed the cancer cells but did not kill the non-transformed cells. The antibodies are characterized for a large number of biochemical parameters and then humanized for therapeutic use.

The melanoma tumor cells isolated and cell lines were cultured as described in Example 1. Balb/c mice were immunized according to the following schedule: 200,000 cells s.c. and i.p. on day 0, then 200,000 cells were injected i.p. on day 21, then 1,000,000 cells were injected on day 49, then 1,250,000 cells in Freund's Complete Adjuvant were injected i.p. on day 107, and then 200,000 cells were injected on day 120 i.p. and then the mice were sacrificed on day 123. The spleens were harvested and the splenocytes were divided into two aliquots for fusion with Sp2/0 (1LN) or NS-1 (2LN) myeloma partners using the methods outlined in example 1.

The screening was carried out 11 days after the fusion against A2058 melanoma cells and CCD-12CoN fibroblasts. Each pair of plates were washed with 100 microliters of room temperature PBS and then aspirated to near dryness. Then 50 microliters of hybridoma supernatant was added to the same wells on each of the two plates. The spent Sp2/0 supernatant was added to the control wells at the same volume and the plates were incubated for around 18 hours at 37 degrees Celsius at a 8% CO$_2$, 98% relative humidity incubator. Then each pair of plates were removed and in the positive control wells 50 microliters of 70% ethanol was substituted for the media for 4 seconds. The plates were then inverted and washed with room temperature PBS once and dried. Then 50 uL of fluorescent live/dead dye diluted in PBS (Molecular Probes Live/Dead Kit) was added for one hour and incubated at 37 degrees Celsius. The plates were then read in a Perkin-Elmer fluorescent plate reader and the data analyzed using Microsoft Excel. The wells that were considered positive were subcloned and the same screening process was repeated 13 days later and then 33 days later. The results of the last screening is outlined in Table 2 below. A number of monoclonal antibodies were produced in accordance with the method of the present invention. These antibodies, whose characteristics are summarized in Table 2, are identified as 1LN-1, 1LN-12, 1LN-14, 2LN-21, 2LN-28, 2LN-29, 2LN-31, 2LN-33, 2LN-34 and 2LN-35. Each of the designated antibodies is produced by a hybridoma cell line having an ATCC Accession Number as follows:

| Antibody | ATCC Accession Number |
|---|---|
| 1LN-1 | |
| 1LN-12 | |
| 1LN-14 | |
| 2LN-21 | |
| 2LN-28 | |
| 2LN-29 | |
| 2LN-31 | |
| 2LN-33 | |
| 2LN-34 | |
| 2LN-35 | |

TABLE 2

Anti-Melanoma Antibodies

% Cell Death

| Clones | Target for Anti-Melanoma Antibodies (A2058) | Normal Fibroblast Cells (CCD-1 2CoN) |
|---|---|---|
| 1LN-1 | 59.4% | <1% |
| 1LN-12 | 55.2% | 1.4% |
| 1LN-14 | 51.4% | <1% |
| 2LN-21 | 72.0% | 15.9% |
| 2LN-28 | 66.6% | 12.4% |
| 2LN-29 | 78.2% | 6.1% |
| 2LN-31 | 100% | 7.8% |
| 2LN-33 | 94.2% | <1% |
| 2LN-34 | 56.6% | 11.2% |
| 2LN-35 | 66.5% | 6.6% |

The table illustrates that clones from both the Sp2/0 and NS-1 fusions were able to produce antibodies that had a greater than 50% killing rate for cancerous cells and at the same time some of the clones were able to produce less than one percent killing of normal control fibroblasts.

The anti-cancer antibodies of the invention are useful for treating a patient with a cancerous disease when administered in admixture with a pharmaceutically acceptable adjuvant, for example normal saline, a lipid emulsion, albumen, phosphate buffered saline or the like and are administered in an amount effective to mediate treatment of said cancerous disease, for example with a range of about 1 microgram per mil to about 1 gram per mil.

The method for treating a patient suffering from a cancerous disease may further include the use of conjugated anti-cancer antibodies and would this include conjugating patient specific anti-cancer antibodies with a member selected from the group consisting of toxins, enzymes, radioactive compounds, and hematogenous cells; and administering these conjugated antibodies to the patient; wherein said anti-cancer antibodies are administered in admixture with a pharmaceutically acceptable adjuvant, for example normal saline, a lipid emulsion, albumen, phosphate buffered saline or the like and are administered in an amount effective to mediate treatment of said cancerous disease, for example with a range of about 1 microgram per mil to about 1 gram per mil. In a particular embodiment, the anti-cancer antibodies useful in either of the above outlined methods may be a humanized antibody.

What is claimed is:

1. The isolated monoclonal antibody produced by the hybridoma deposited with the ATCC as Accession Number PTA-2698.

2. A humanized version of the isolated monoclonal antibody of claim 1, which specifically binds to the antigen to which said monoclonal antibody binds.

3. The isolated hybridoma deposited with the ATCC as Accession Number PTA-2698.

4. An antigen-binding fragment of the isolated monoclonal antibody of claim 1.

5. An antigen-binding fragment of the humanized antibody of claim 2.

6. The isolated monoclonal antibody, humanized antibody, or antigen binding fragment of any one of claims 1, 2, 4 and 5 conjugated with a member selected from the group consisting of a cytotoxic moiety, an enzyme and a radioactive compound.

* * * * *